United States Patent
Kopelman et al.

(10) Patent No.: US 12,329,560 B2
(45) Date of Patent: Jun. 17, 2025

(54) SYSTEMS FOR GUIDING DENTAL IMAGING

(71) Applicant: Align Technology, Inc., San Jose, CA (US)

(72) Inventors: Avi Kopelman, Palo Alto, CA (US); Michael Sabina, San Jose, CA (US)

(73) Assignee: Align Technology, Inc., San Jose, CA (US)

( * ) Notice: Subject to any disclaimer, the term of this patent is extended or adjusted under 35 U.S.C. 154(b) by 380 days.

(21) Appl. No.: 17/701,611

(22) Filed: Mar. 22, 2022

(65) Prior Publication Data
US 2022/0296184 A1 Sep. 22, 2022

Related U.S. Application Data

(60) Provisional application No. 63/164,508, filed on Mar. 22, 2021.

(51) Int. Cl.
| | |
|---|---|
| *A61B 6/51* | (2024.01) |
| *A61B 5/00* | (2006.01) |
| *A61B 6/00* | (2006.01) |
| *A61C 9/00* | (2006.01) |

(52) U.S. Cl.
CPC ............ *A61B 6/512* (2024.01); *A61B 5/0066* (2013.01); *A61B 5/0088* (2013.01); *A61B 6/488* (2013.01); *A61B 6/5247* (2013.01); *A61C 9/0086* (2013.01)

(58) Field of Classification Search
CPC ..... A61B 6/512; A61B 5/0066; A61B 5/0088; A61B 6/488; A61B 6/5247; A61B 6/4429; A61C 9/0086
See application file for complete search history.

(56) References Cited

U.S. PATENT DOCUMENTS

| | | |
|---|---|---|
| 6,099,314 A | 8/2000 | Kopelman et al. |
| 6,334,772 B1 | 1/2002 | Taub et al. |
| 6,334,853 B1 | 1/2002 | Kopelman et al. |
| 6,463,344 B1 | 10/2002 | Pavloskaia et al. |
| 6,542,249 B1 | 4/2003 | Kofman et al. |
| 6,633,789 B1 | 10/2003 | Nikolskiy et al. |
| 6,664,986 B1 | 12/2003 | Kopelman et al. |
| 6,697,164 B1 | 2/2004 | Babayoff et al. |

(Continued)

FOREIGN PATENT DOCUMENTS

| | | |
|---|---|---|
| WO | 2020142397 A1 | 7/2020 |
| WO | 2020142404 A1 | 7/2020 |

OTHER PUBLICATIONS

Wu et al., "C-arm orbits for metal artifact avoidance (MAA) in cone-beam CT," Physics in Medicine and Biology, Institute of Physics Publishing, Aug. 14, 2020, vol. 65(16):165012, pp. 1-16, XP020355797, ISSN: 0031-9155, DOI: 10.1088/1361-6560/AB9454 [retrieved on Aug. 14, 2020].

*Primary Examiner* — Dani Fox
*Assistant Examiner* — Mamadou Faye
(74) *Attorney, Agent, or Firm* — Shay Glenn LLP (57) ABSTRACT

Methods and apparatuses for positioning of dental imaging devices, such as X-rays, CTs and ultrasound imaging devices. These methods and apparatuses may use an initial intraoral scan of a patient's dentition taken, e.g., using a visible light and/or infrared source, and generate an imaging plan and/or guide(s) for taking one or more penetrative images, such as X-ray images, of the patient's dentition using the intraoral scan data.

10 Claims, 4 Drawing Sheets

(56) References Cited

U.S. PATENT DOCUMENTS

| | | |
|---|---|---|
| 6,845,175 B2 | 1/2005 | Kopelman et al. |
| 6,979,196 B2 | 12/2005 | Nikolskiy et al. |
| 7,030,383 B2 | 4/2006 | Babayoff et al. |
| 7,202,466 B2 | 4/2007 | Babayoff et al. |
| 7,255,558 B2 | 8/2007 | Babayoff et al. |
| 7,286,954 B2 | 10/2007 | Kopelman et al. |
| 7,319,529 B2 | 1/2008 | Babayoff |
| 7,373,286 B2 | 5/2008 | Nikolskiy et al. |
| 7,507,088 B2 | 3/2009 | Taub et al. |
| 7,545,372 B2 | 6/2009 | Kopelman et al. |
| 7,698,068 B2 | 4/2010 | Babayoff |
| 7,916,911 B2 | 3/2011 | Kaza et al. |
| 8,108,189 B2 | 1/2012 | Chelnokov et al. |
| 8,244,028 B2 | 8/2012 | Kuo et al. |
| 8,587,582 B2 | 11/2013 | Matov et al. |
| 8,948,482 B2 | 2/2015 | Levin |
| D742,518 S | 11/2015 | Barak et al. |
| 9,192,305 B2 | 11/2015 | Levin |
| 9,261,356 B2 | 2/2016 | Lampert et al. |
| 9,261,358 B2 | 2/2016 | Atiya et al. |
| 9,299,192 B2 | 3/2016 | Kopelman |
| D760,901 S | 7/2016 | Barak et al. |
| 9,393,087 B2 | 7/2016 | Moalem |
| 9,408,679 B2 | 8/2016 | Kopelman |
| 9,431,887 B2 | 8/2016 | Boltanski |
| 9,439,568 B2 | 9/2016 | Atiya et al. |
| 9,451,873 B1 | 9/2016 | Kopelman et al. |
| D768,861 S | 10/2016 | Barak et al. |
| D771,817 S | 11/2016 | Barak et al. |
| 9,491,863 B2 | 11/2016 | Boltanski |
| D774,193 S | 12/2016 | Makmel et al. |
| 9,510,757 B2 | 12/2016 | Kopelman et al. |
| 9,660,418 B2 | 5/2017 | Atiya et al. |
| 9,668,829 B2 | 6/2017 | Kopelman |
| 9,675,430 B2 | 6/2017 | Verker et al. |
| 9,693,839 B2 | 7/2017 | Atiya et al. |
| 9,717,402 B2 | 8/2017 | Lampert et al. |
| 9,724,177 B2 | 8/2017 | Levin |
| 9,844,426 B2 | 12/2017 | Atiya et al. |
| 10,076,389 B2 | 9/2018 | Wu et al. |
| 10,098,714 B2 | 10/2018 | Kuo |
| 10,108,269 B2 | 10/2018 | Sabina et al. |
| 10,111,581 B2 | 10/2018 | Makmel |
| 10,111,714 B2 | 10/2018 | Kopelman et al. |
| 10,123,706 B2 | 11/2018 | Elbaz et al. |
| 10,136,972 B2 | 11/2018 | Sabina et al. |
| 10,380,212 B2 | 8/2019 | Elbaz et al. |
| 10,390,913 B2 | 8/2019 | Sabina et al. |
| 10,453,269 B2 | 10/2019 | Furst |
| 10,456,043 B2 | 10/2019 | Atiya et al. |
| 10,499,793 B2 | 12/2019 | Ozerov et al. |
| 10,504,386 B2 | 12/2019 | Levin et al. |
| 10,507,087 B2 | 12/2019 | Elbaz et al. |
| 10,517,482 B2 | 12/2019 | Sato et al. |
| 10,695,150 B2 | 6/2020 | Kopelman et al. |
| 10,708,574 B2 | 7/2020 | Furst et al. |
| 10,772,506 B2 | 9/2020 | Atiya et al. |
| 10,813,727 B2 | 10/2020 | Sabina et al. |
| 10,888,399 B2 | 1/2021 | Kopelman et al. |
| 10,952,816 B2 | 3/2021 | Kopelman |
| 10,980,613 B2 | 4/2021 | Shanjani et al. |
| 11,013,581 B2 | 5/2021 | Sabina et al. |
| D925,739 S | 7/2021 | Shalev et al. |
| 11,096,765 B2 | 8/2021 | Atiya et al. |
| 11,238,586 B2 | 2/2022 | Minchenkov et al. |
| 11,367,192 B2 | 6/2022 | Kopelman et al. |
| 2017/0273654 A1* | 9/2017 | Taguchi ............... A61B 6/035 |
| 2019/0029784 A1 | 1/2019 | Moalem et al. |
| 2019/0231492 A1* | 8/2019 | Sabina ................ A61C 7/002 |
| 2019/0388193 A1 | 12/2019 | Saphier et al. |
| 2020/0281702 A1 | 9/2020 | Kopelman et al. |
| 2020/0315434 A1 | 10/2020 | Kopelman et al. |
| 2020/0349705 A1 | 11/2020 | Minchenkov et al. |
| 2020/0404243 A1 | 12/2020 | Saphier et al. |
| 2020/0405154 A1* | 12/2020 | Moghaddam ........ A61B 5/0035 |
| 2021/0030503 A1 | 2/2021 | Shalev et al. |
| 2021/0059796 A1 | 3/2021 | Weiss et al. |
| 2021/0068773 A1 | 3/2021 | Moshe et al. |
| 2021/0121049 A1 | 4/2021 | Rudnitsky et al. |
| 2021/0128281 A1 | 5/2021 | Peleg |
| 2021/0137653 A1 | 5/2021 | Saphier et al. |
| 2021/0196152 A1 | 7/2021 | Saphier et al. |
| 2022/0225952 A1* | 7/2022 | Turner ................. A61B 6/512 |

\* cited by examiner

SYSTEMS FOR GUIDING DENTAL IMAGING

CLAIM OF PRIORITY

This patent application claims priority to U.S. Provisional Patent Application No. 63/164,508, titled "SYSTEMS AND METHODS FOR GUIDING DENTAL IMAGING," filed on Mar. 22, 2021, herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Dental imaging of internal tooth structures, such as x-rays, are commonly used in the field of dentistry for diagnosis and treatment of the oral cavity. X-rays are able to portray the structural integrity of teeth and supporting tissues if exposed correctly. Other penetrative imaging techniques include ultrasound and specific types of x-rays, such as cone beam computed tomography (CT) scanning. It is important that penetrative images such as x-rays are correctly exposed so as to ensure that a patient receives proper diagnosis and treatment. In addition, the use of ionizing radiation, such as x-rays, for imaging should be minimized, therefore it is also important to avoid taking having to re-take additional images.

Proper exposure can be difficult to achieve, however, because of distortions that can occur during exposure. For example, if an x-ray is not properly positioned when exposed, it can distort or hide the relevant area being radiographed. An inaccurate x-ray can lead to improper diagnosis and treatment by the dental practitioner, which can result in significant harm to the patient by causing a practitioner to wrongfully believe that more or less treatment is needed than actually required.

In view of the foregoing, there is an ongoing need for improved positioning of dental penetrative imaging devices such as x-ray devices. Such improvements would lead to more efficient diagnosis and treatment by dental practitioners. The methods and apparatuses (e.g., devices, systems, etc.) described herein may address this need.

SUMMARY OF THE DISCLOSURE

The methods and apparatuses described herein are related to positioning of dental imaging devices, such as X-rays, CTs and ultrasound imaging devices.

For example, described herein are methods and apparatuses for positioning of dental imaging devices, such as X-rays, CTs and ultrasound imaging devices. These methods and apparatuses (e.g., devices, systems, etc.) may use an initial intraoral scan of a patient's dentition, e.g., taken by an intraoral scanner using visible and/or infrared light, and may generate an imaging plan for taking one or more secondary images, such as X-ray images, of the patient's dentition. Secondary images may be taken with an ionizing radiation. The imaging plan may include what angle(s) to align or position the penetrative imaging device and/or one or more frames, gantries, holders, or the like, which is collectively referred to herein as a guide or guide device, to position the imaging device relative to the patient's dentition (e.g., teeth). For example, these methods and apparatuses may include designing, building and/or using a guide that may be held in, on, or against the patient's teeth for positioning the penetrative imaging apparatus.

In some examples the methods and apparatuses described herein may be used following a scanner or scanning device such as an intraoral scanner. The intraoral scanner may be a handheld intraoral scanner and may image the patient's dentition, such as one or more of the patient's teeth, gingiva, dental arch (upper and/or lower), palate, etc. The intraoral scanner may generate a collection of images of the patient's dentition and/or a 3D model of the patient's dentition. For example, the intraoral scanner may generate a model of the patient's dentition that is a three-dimensional (3D) digital model of the surface of the patient's teeth. In some examples the intraoral scanner may generate a 3D volumetric model of the patient's teeth that include internal structures. For example, the intraoral scan may include infrared (e.g., IR, near-IR, etc.) scanning of the patient's teeth, from which a 3D volumetric model may be constructed.

The non-penetrative scan of the patient's teeth taken with the intraoral scanner may be used to generate an imaging plan and/or a guide that provides instructions on which positions, orientations and/or directions one or more penetrative image(s) should be taken from. For example, an intraoral scanner, such as the iTero™ scanner, may be used to scan the patient's intraoral cavity, including the teeth. The resulting non-penetrative scan may be used, either locally as part of the scanning system, or remotely using a remote server, to generate a set of imaging recommendations including, for example, which penetrative scan (e.g., X-ray) should be taken, including in some examples, which type of penetrative imaging (e.g., CT scan, ultrasound scan, etc.) should be used, at which angle(s) the penetrative image should be taken (e.g., how to align the penetrative imaging machine), and/or other parameters that should be used in taking the penetrative image(s), such as, e.g., the size and location of the sensor, the intensity (e.g., Xray intensity), and the like. Any of these methods may also generate one or more guides to assist in performing the penetrative scan as determine by the imaging plan. In some examples the imaging plan is or includes the design of the guide. Examples of guides are provided herein and may include a bite block or other tooth-worn region for securing or otherwise guiding a penetrative imaging device (e.g., sensor) or system.

Thus, any of these methods and apparatuses may include automatically or after a user requests, providing a recommended penetrative imaging plan which may be or may include one or more guides for taking one or more penetrative images. The penetrative imaging plan may be provided at the dental practitioner's office immediately following performing the intraoral scan, or it may be performed using a stored intraoral scan, e.g., taken hours, days, weeks or years before taking the penetrative image(s). For example, a user (e.g., a dental professional, clinician, etc.) may request a recommendation and/or guide for the best method to take penetrative scans, e.g., that may demonstrate features (e.g., lesions) in the patient's dentition using one or more additional diagnostic technique such as a penetrative image, including but not limited to x-rays and the like (e.g., ultrasound).

In general, the non-penetrative intraoral scan may be used to generate an imaging plan (e.g., a penetrative imaging plan) since the intraoral scan may provide locations for the teeth relative to each other, including precise locations of external dental features and/or (e.g., with near-IR imaging) internal features. The methods and apparatuses described herein may use the intraoral scans (either directly in some examples or after forming a 3D model) to determine orientations for the penetrator imaging device or system, e.g., based on the 3D structure location and volume of the findings. The imaging plan and/or guide may be configured to avoid obstacles that may interfere with the penetrative imaging (e.g., X-ray), such as object's in or on the teeth that might be in the way (e.g., metal implants, metal fillings and PFM crowns, etc.). The imaging plans may be configured to minimize the number of penetrative images (e.g., minimize the number of X-ray images) in order to capture the most information in each image.

These methods and apparatuses may be configured to consider clinician-specific needs in determining the imaging plan. For example, the apparatus or method may figure the distance between the carries to the dentin. In some examples, the methods and/or apparatuses described herein may be configured (or selected, e.g., by a user) to capture interproximal areas between two or more adjacent teeth.

As mentioned, any of these methods and apparatuses may include using the imaging plan to determine orientation data to design and or generate (e.g., ay 3D printing, custom fitting, etc.) patient-specific, guides, which may include a bite block to ensure technicians capture the desired image using a particular penetrative imaging technique (e.g., x-ray). As mentioned, these apparatuses and methods are not limited to preparing imaging plans for a specific imaging modality. In some examples the imaging modality is a penetrative imaging modality, such as (but not limited to) X-ray, ultrasound and/or CT scanning.

The methods described herein may also be used to generate a guide; as described above, the guide may comprise a jig for holding the penetrative imaging (e.g., x-ray) sensor in a position determined by the method and/or apparatus based on the intraoral scan. The guide (e.g., jig) may be a custom-made tool used to control the location, orientation and/or motion of the penetrative imaging senor. Any of these guides may be configured to be held in the patient's mouth, e.g., between the patient's teeth, and may be oriented by teeth or other regions of the oral cavity.

Thus, described herein are methods, including a method comprising: receiving a scan of a patient's dentition; identifying, from the scan or more of: a position of the patient's teeth and a position of a dental restoration; determining one or more positions for orienting a penetrative imaging apparatus for taking a penetrative scan of the patient's teeth (e.g., an x-ray apparatus for x-raying the patient's teeth) in order to avoid interference from one or more of: adjacent teeth and the dental restoration, using the scan; and guiding a user in taking one or more penetrative image (e.g., x-rays) using the determined one or more positions for orienting a penetrative imaging (e.g., an x-ray) apparatus.

For example, a method may include: receiving a scan of a patient's dentition, wherein the scan comprises a near-IR scan; identifying, from the scan, tooth position and one or more of: a dental lesion and a dental restoration; determining one or more positions for orienting an x-ray apparatus for x-raying the patient's teeth, including an identified dental lesion, in order to avoid interference from the dental restoration and/or an adjacent tooth, using the scan; and guiding a user in taking one or more x-rays using the determined one or more positions for orienting an x-ray apparatus.

Any of these methods may include receiving an intraoral scan. For example, receiving the scan of the patient's dentition may include receiving an intraoral scan. Receiving the scan of the patient's dentition may include receiving an intraoral scan comprising one or more of: a near-infrared (near-IR) scan of the patient's dentition, an ultrasound scan of the patient's dentition, and an optical coherence tomography (OCT) scan of the patient's dentition.

In some examples, the method may include scanning the patient's dentition with an intraoral scanner. For example, scanning the patient's dentition with an intraoral scanner to take a near-infrared (near-IR) scan of the patient's dentition.

In any of these methods identifying may include identifying a location of one or more dental lesions and wherein determining one or more positions for orienting the penetrative imaging apparatus comprises using the location of the one or more lesions to maximize an image of the one or more lesions in a penetrative (e.g., x-ray) image taken using the one or more positions.

Determining one or more positions for orienting an x-ray apparatus may include determining a minimum number of images (e.g., x-ray images) to take in order to capture images of all of the patient's teeth.

As mentioned above, any of these methods and apparatuses performing them may include using a guide (e.g., a jig). For example, guiding a user in taking one or more penetrative images (e.g., x-rays) may include determining a configuration for a bite block for holding the guide (e.g., jig) by the patient's teeth in a determined orientation.

Guiding a user in taking one or more penetrative images (e.g., x-rays) may include comprises robotically controlling the penetrative imaging apparatus.

Also described herein are systems for performing any of the methods described herein. For example, a system may include: one or more processors; a memory coupled to the one or more processors, the memory configured to store computer-program instructions, that, when executed by the one or more processors, perform a computer-implemented method comprising: receiving a scan of a patient's dentition; identifying, from the scan or more of: a position of the patient's teeth and a position of a dental restoration; determining one or more positions for orienting an x-ray apparatus for x-raying the patient's teeth in order to avoid interference from one or more of: adjacent teeth and the dental restoration, using the scan; and guiding a user in taking one or more x-rays using the determined one or more positions for orienting an x-ray apparatus.

In some examples a system may include: one or more processors; a memory coupled to the one or more processors, the memory configured to store computer-program instructions, that, when executed by the one or more processors, perform a computer-implemented method comprising: receiving a scan of a patient's dentition, wherein the scan comprises a near-IR scan; identifying, from the scan, tooth position and one or more of: a dental lesion and a dental restoration; determining one or more positions for orienting an x-ray apparatus for x-raying the patient's teeth, including an identified dental lesion, in order to avoid interference from the dental restoration and/or an adjacent tooth, using the scan; and guiding a user in taking one or more x-rays using the determined one or more positions for orienting an x-ray apparatus. As mentioned above, receiving the scan of the patient's dentition may include receiving an intraoral scan.

In any of these systems, receiving the scan of the patient's dentition may include receiving an intraoral scan comprising one or more of: a near-infrared (near-IR) scan of the patient's dentition, an ultrasound scan of the patient's dentition, and an optical coherence tomography (OCT) scan of the patient's dentition.

Any of these systems may be configured to scan the patient's dentition with an intraoral scanner. Thus, any of these systems may include (or be part of) an intraoral scanner. For example, a system may be configured to scan the patient's dentition with an intraoral scanner to take a near-infrared (near-IR) scan of the patient's dentition.

Identifying may include identifying a location of one or more dental lesions and wherein determining one or more positions for orienting the x-ray apparatus comprises using the location of the one or more lesions to maximize an image of the one or more lesions in an x-ray image taken using the one or more positions. The systems described herein may be configured to determine one or more positions for orienting an x-ray apparatus by determining a minimum number of x-ray images to take in order to capture images of all of the patient's teeth.

Any of these systems may include a guide, including one or more jigs for guiding a user in taking one or more penetrative images (such as, but not limited to, x-rays), which may include determining a configuration for a bite block. Thus, the jig(s) may include one or more regions configured to conform to match a patient's teeth so that the jig may be held in a predetermined position when bitten by the patient.

Any of the systems described herein may be robotic systems. For example, the system may be configured so that, e.g., guiding a user in taking one or more x-rays comprises robotically controlling the x-ray apparatus.

In some variations the method and apparatuses described herein may also or alternatively be configured to provide a treatment plan that is configured to apply one or more compositions (e.g., drug compositions, therapeutics, etc.) for localized specific treatment. For example, the methods described herein may be used to define one or more locations within the oral cavity to treat using different drugs. In one example, the intraoral scan may be analyzed to determine the location of damage on the enamel of the patient's teeth. The methods and apparatuses described herein may be adapted to design and/or build an aligner or series of aligners that may deliver a therapeutic in that area to specifically, and locally, treat the damage. All of the methods and apparatuses described herein, in any combination, are herein contemplated and can be used to achieve the benefits as described herein.

BRIEF DESCRIPTION OF THE DRAWINGS

A better understanding of the features and advantages of the methods and apparatuses described herein will be obtained by reference to the following detailed description that sets forth illustrative embodiments, and the accompanying drawings of which.

DETAILED DESCRIPTION

The methods and apparatuses described herein may include using an intraoral scan to form an imaging plan for taking one or more (e.g., a set of) penetrative images of a patient's teeth, such as X-rays (including but not limited to CT-scans) and ultrasound. In particular, a non-ionizing (and in some cases non-penetrative) intraoral scan may be used to generate an imaging plan and/or guide, which may include one or more of: a set of recommendations, including which imagines should be taken, in what angle to align the imaging device, and/or other parameters (e.g., size and location of the sensor, imaging intensity, etc.); a plan for one or more guides (e.g., jigs) and/or one or more guides (e.g., jigs).

Thus, in some examples, these methods may include or be subsequent to taking an intraoral scan (e.g., or may receive an already-taken intraoral scan) of a patient, and may recommend (automatically and/or following a clinician request) an imaging plan based on the intraoral scan that indicates an orientation and/or position of an imaging device (e.g., an x-ray imaging device), based on one or more of: the three-dimensional (3D) structure location and volume of the patient's teeth, avoiding one or more obstacles that may interfere with the imaging (e.g., X-ray) that might be in the way, such as metal implants, metal fillings and PFM crowns; minimizes the number of X-ray images in order to capture the most information in each scan; and/or considers the clinician-specific needs, for example, figures the distance between the carries to the dentin, interproximal regions, etc. Any of these methods and apparatuses may also or alternatively use the orientation data to design and/or form (e.g., by 3D printing) custom fit, patient specific, jigs (e.g., including bite blocks) to ensure the capture the desired image(s).

As used herein, a patient may be a subject, including human or non-human (e.g., animal) subjects, having teeth to be imaged. The images may be digital images and may be separate from or combined with the intraoral scanning data. The user may be dental technician and/or a dental professional, such as a dentist, orthodontist, doctor, etc.

Figure 1:
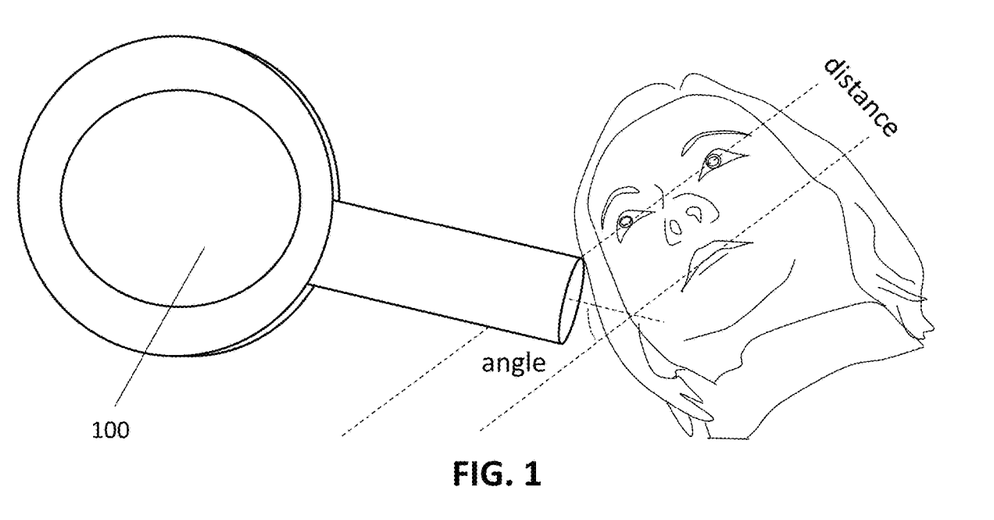
FIG. 1 is an example of a penetrative imaging device (e.g., x-ray imaging device) configured to take one or more images of the patient's teeth.

FIG. 1 illustrates one example of a typical apparatus 100 for taking X-ray images of a patient's teeth. As shown, the device may be configured to adjust the orientation of the x-ray sensor(s) relative to the patient, including adjusting the angle and/or distance from the patient's mouth. The imaging device may be mounted or attached to a gantry that allows its relative position and orientation to be adjusted.

Figure 2:
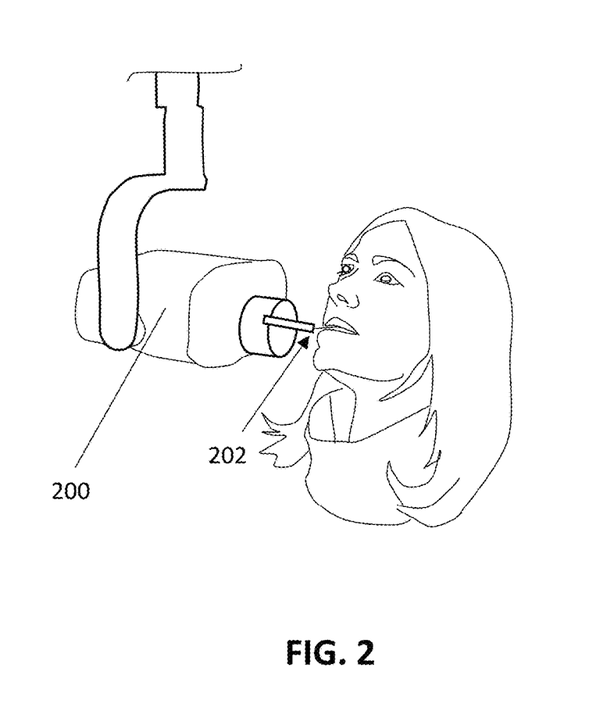
FIG. 2 is an example of a penetrative imaging device used in conjunction with a guide (e.g., jig) held in the patient's teeth to direct the penetrative imaging device.

In some cases, it may be beneficial to more precisely position the imaging device relative to the patient's teeth, for example, by using a guide (e.g., jig) including a bite-block for controlling the relative position and/or orientation of the imaging device relative to the teeth. For example, in FIG. 2 an imaging device (e.g., X-ray device 200), similar to that shown in FIG. 1, is used with a guide 202. The guide is gripped in the patient's teeth in this example and attached to the imaging device. Thus, a distal end region of the imaging device may be held and/or positioned by the guide at a predetermined distance from the patient's teeth, as shown. The guide in FIG. 2 may include a protective cover (e.g., a thin polymeric sleeve) that fits over the guide.

In some examples, the systems and methods described herein may receive and/or may assist in taking an intraoral scan of the patients' teeth. For example, an intraoral scan may be taken using an intraoral scanner, such as the iTERO™ intraoral scanner from Align Technologies. In some cases, the intraoral scanner may generate a set of images of the patient's intraoral cavity and/or a digital model of the patient's teeth, gingiva and/or palate. This scan data (the images and/or digital model) may be used to generate one or more specific imaging plans for imaging the patient's teeth to optimally capture one or more specific features (e.g., caries, regions of occlusion, interproximal regions, etc.). In any of these methods and apparatuses, the apparatus may generate a design for a guide, and/or may generate the guide.

Figure 3:
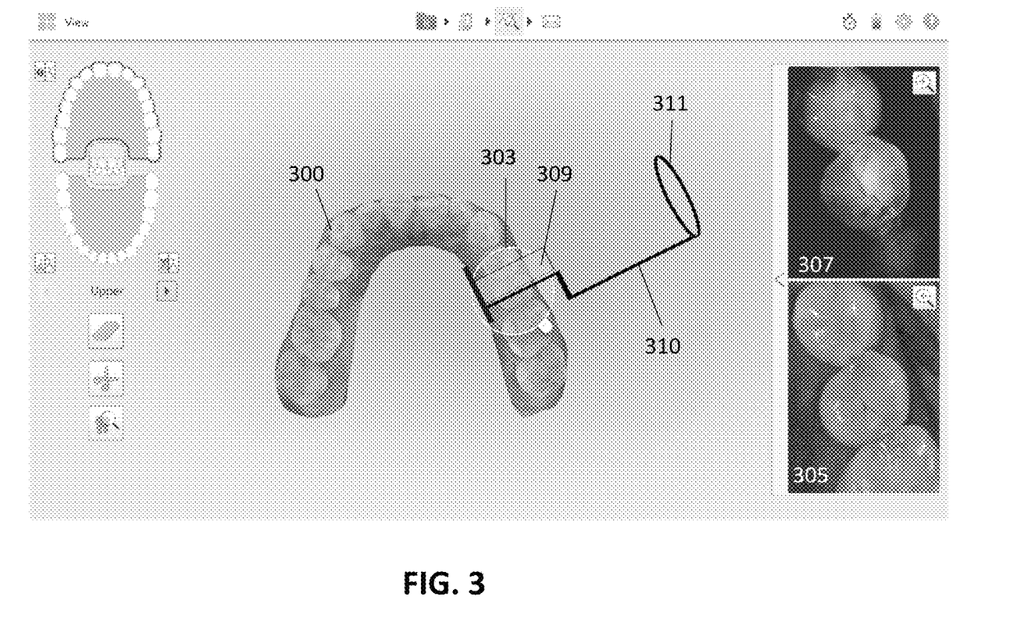
FIG. 3 is an example of a virtual X-Ray position guide derived form an intraoral scan, as described herein. This imaging plan may be used to generate one or more custom guides (e.g., jigs) including a patient-specific bite block.

For example, FIG. 3 shows one example of a user interface for a system that receives and/or takes and intraoral scan of the patient's dentition. In FIG. 3, the intraoral scan includes a 3D model of the patient's dentition 300 (shown as the upper arch in this example). In this example, both a surface (e.g., visible light) and an infrared (e.g., near-IR) scan is taken and used by the system. In FIG. 3, a selected region (shown by loop 303) is shown including corresponding surface 305 and near-IR 307 images. The apparatus (e.g., the system) uses the intraoral scan to determine a virtual angle and position from the teeth to take one or more images of the teeth using a penetrative imaging device, such as an x-ray device. The apparatus may determine the optimal position and orientation based on one or more specified features to capture (e.g., caries, interproximal spaces, etc.) and/or features to avoid (e.g., fillings, overlapping teeth, etc.). The optimal position may maximize the view of the features to be captured or included, while minimizing the view of features to be avoided. The steps of determining the optimal position may be determined by modeling one or more virtual images through the teeth and ranking/scoring them. The highest-ranked/scored images may then be proposed as part of an imaging plan.

Once the system has determined one or more (e.g., optimal) views, including the angle and/or distance from the imaging sensor to the teeth, the system may then generate one or more guides to achieve these views. For example, as shown in FIG. 3, a guide 311 may be generated including a customized bite block region 309 that is configured to be held by a specific portion or region of the teeth, in a specific orientation, as well as a frame 310 that include a support ring 311 for engaging the distal end of the imaging sensor (e.g., x-ray device), similar to that shown in FIG. 2.

Any of these guides (e.g., jigs) may include a bite block region that is configured so that it may mate with a particular portion of the patient's teeth from the upper and lower jaws, so that it may be held in a particular orientation. Further, the bite block may be configured to hold the lower jaw in a predetermined position relative to the upper jaw that is different from the patient's usual bite (intercuspation). Thus, the guide (e.g., jig) may hold the lower jaw in a position relative to the upper jaw so as to optimize the image taken when using the guide.

The end region of the guide typically includes an engagement region for engaging with the imaging device (e.g., x-ray sensor). This engagement region may be a ring or other structure into which the imaging device may fit. The engagement region may include a lock, clasp, clamp, etc. or other releasable attachment for releasably securing to the imaging device, in order to hold it in position. In FIG. 3 the engagement region is shown as a ring.

In some examples, the method and/or systems described herein may provide specification for fabricating the one or more guides. For example, the design specifics, e.g., measurements, dimensions, etc., may be provided as a digital output file that may be provided to allow manual or automatic fabrication of the guide(s). In some examples the systems and methods may fabricate the guide(s). For example, the guides may be fabricated by 3D printing.

Figure 4:
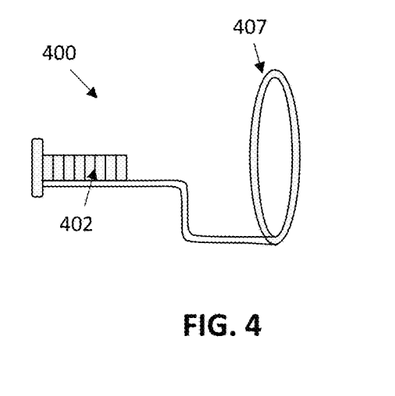
FIG. 4 schematically illustrates one example of a guide including a generic bite block.
Figure 5:
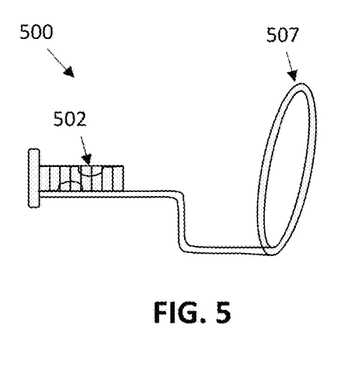
FIG. 5 schematically illustrates one example of a patient-specific guide including a patient-specific bite block.

FIG. 4 shows an example of a typical (non-customized) guide 400 that includes a bite block region 402 and an engagement region 407. As mentioned, the guide may be customized by the methods and systems described herein, using intraoral scan data. For example, FIG. 5 illustrates one example of a patient-specific guide 500 that is customized to the patient so that it includes a bite block region 502 that is configured to engage with a specific portion of the upper arch and lower arch and to hold the engagement region 507 in a predefined orientation so that when an imaging sensor is engaged with the engagement region it may take an image of the teeth that has been precalculated as described above.

Figure 6A:
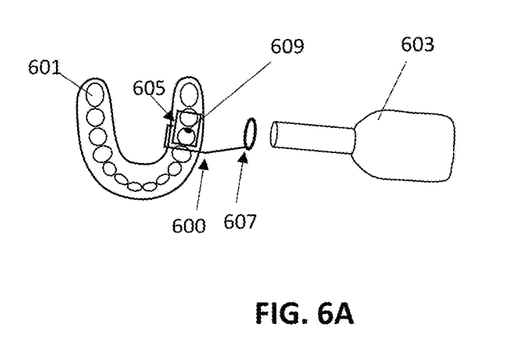
FIGS. 6A-6B illustrate an example of a method of using a guide to direct taking of a penetrative image of the patient's teeth when the guide is secured by the teeth.
Figure 6B:
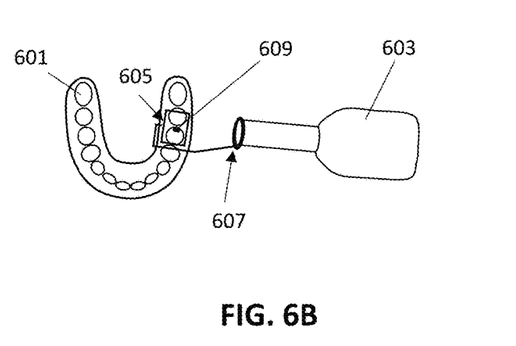

FIGS. 6A-6B illustrate one example of a method of engaging an imaging sensor 603 with an engagement region 607 of a guide 600. In this example, which (for simplicity) shows only the lower dental arch, the patient-specific bite block 605 may be held between the teeth in a particular, predefined manner by the teeth, which holds the engagement region 607 in a predefined orientation. The imaging sensor is shown engaged with the guide in FIG. 6B, setting the orientation and distance to the teeth. In FIGS. 6A-6B a particular feature 609 of the teeth, e.g., carries), is shown; the guide may be configured to optimize the image of this feature, as described above.

In general, the methods described herein may be methods of imaging the patient's dentition, and/or methods of forming a guide for imaging the patient's dentition, and/or method of forming an imaging plan to take one or more images of a patient's dentition. Similarly, the apparatuses described herein may apparatuses for forming an imaging plan, apparatuses for imaging a patient's dentition, apparatuses for forming a guide (e.g., jig), and/or the guide itself.

Figure 7:
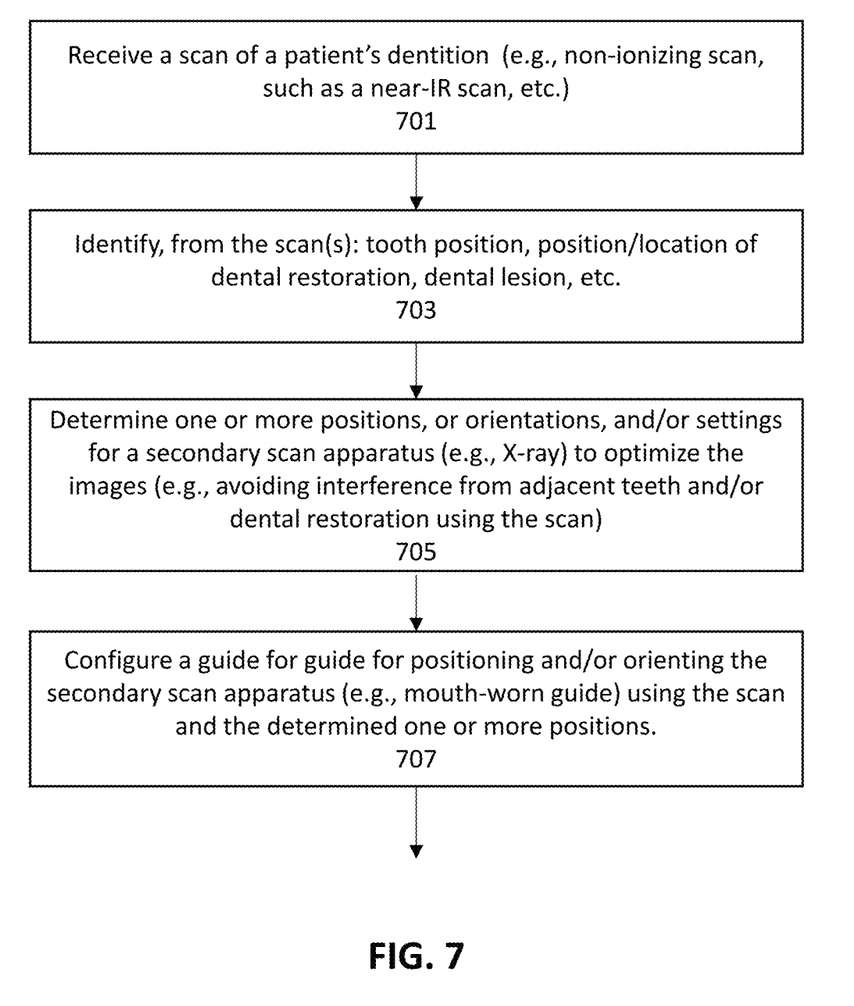
FIG. 7 shows one example of a method as described herein.

For example, FIG. 7 illustrates one method as described herein, showing a method of forming an imaging plan, which includes designing and/or forming a guide for taking one or more images.

In any of these methods a scan of the patient's dentition, which may include both the patient's upper and lower dental arch is received 701. The intraoral scan may already have been taken from the patient and may be retrieved and/or accessed by the system, or it may be taken as part of the method. In some examples the method may be performed by a device that is local to the patient; the dental professional may first scan the patient's dentition, e.g., using an intraoral scanner, and may, while the patient is still present (as part of the same treatment session) use an apparatus to perform the method to generate an imaging plan for taking additional images (e.g., penetrative, such as X-ray) images of the patient's teeth.

In some examples the system for generating the imaging plan may be integrated with, coupled to and/or part of the intraoral scanning system. The system for generating the imaging plan may access the intraoral scan data directly via a connection to the intraoral scanner, or it may receive the intraoral scan data from a remote site (e.g., server), or the like. The intraoral scan is typically performed with non-ionizing radiation, such as visual light and/or infrared light (e.g., near-IR light). The penetrative imaging may be performed with an ionizing radiation (such as x-ray).

Once the scan has been received and/or accessed, the system may identify one or more obstacles to avoid and/or one or more targets to capture in the secondary imaging. The method may include identifying from the intraoral scan data the tooth position(s), the position/location of one or more dental restoration (e.g., filling, etc.), the position/location of one or more dental lesions (e.g., cavities, etc.) 703. In some examples, the system may receive (e.g., via a user interface) instructions from the user about which features or targets to optimize, such as interproximal spaces, lesions, etc. The system may detect these features or targets automatically, semi-automatically or manually, e.g., using the intraoral scan data. In some examples the system may present the intraoral scan data to the user (e.g., using a user interface, such as the user interface shown in FIG. 3, above), and the user may select the one or more features to optimize during the secondary imaging.

The method may then determine one or more positions and/or orientations and/or settings for the secondary image(s), e.g., x-rays, in order to optimally capture the target feature(s) and avoid interference form obstacles 705. For example, the methods may include determining one or more positions and/or orientations, and/or settings for a secondary scan apparatus (e.g., X-ray) to avoid interference from adjacent teeth and/or dental restoration using the intraoral scan data.

Thus, the method may generate an imaging plan and/or or more guides to take the secondary images 707. In some examples, the method may include configuring a guide, such as a jig, for positioning and/or orienting the secondary scan apparatus using the intraoral scan data and the determined one or more positions, e.g., of the teeth and/or obstacles and/or targets. In some examples creating a guide include creating a jig that includes a bite block region that is specifically configured to be held at a particular region of the patient's teeth. The bite block may be configured to be held between the upper and lower arches when the patient bites down onto the bite block. The bite block may include receiving cavities configured to receive the patient's teeth so that it is matched to a region of the teeth. In some examples the bite block may match regions of both the upper and lower teeth. The guide may also include an engagement region that is connected (e.g., via an elongate member) to the bite block. The method may set the length, shape and/or orientation of the elongate member and/or the engagement region so that it holds the distal end of the imaging sensor (e.g., x-ray sensor) in a predefined position that allows the imaging sensor to capture the image calculated by the method from the intraoral scan.

In some examples, the method may include fabricating the guide or transmitting instructions (e.g., specifications) for fabricating the guide. The instructions or specifications may be digital, for review and execution by an automated fabrication device (e.g., 3D printer, etc.) or they may be manual. In some examples the bite block region may be fabricated by a 3D printer or other device, while the elongate member and/or the engagement region may be combined with the bite block manually, semi-automatically or automatically using the instructions.

The method may also optionally include taking the secondary images of the patient's dentition using the guide(s) and/or imaging plan. For example, the method may include taking one or more images and storing the images as part of a patient's dental record(s).

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits described herein.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like. For example, any of the methods described herein may be performed, at least in part, by an apparatus including one or more processors having a memory storing a non-transitory computer-readable storage medium storing a set of instructions for the processes(s) of the method.

While various embodiments have been described and/or illustrated herein in the context of fully functional computing systems, one or more of these example embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. In some embodiments, these software modules may configure a computing system to perform one or more of the example embodiments disclosed herein.

As described herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively or in combination, the processor can be configured to combine one or more steps of one or more methods as disclosed herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A system comprising:
   one or more processors;
   a memory coupled to the one or more processors, the memory configured to store computer-program instructions, that, when executed by the one or more processors, perform a computer-implemented method comprising:
   receiving a non-penetrating scan of a patient's dentition;
   determining a three-dimensional (3D) model of the patient's dentition based on the non-penetrating scan;
   identifying, from the 3D model one or more of: a position of a patient's teeth and a position of a dental restoration;
   determining, using the 3D model, one or more positions for orienting an x-ray apparatus for x-raying the patient's teeth in order to avoid interference from one or more of: adjacent teeth and the dental restoration; and
   guiding a user in taking one or more x-rays using the determined one or more positions for orienting an x-ray apparatus.

2. The system of claim 1, wherein receiving the scan of the patient's dentition comprises receiving an intraoral scan.

3. The system of claim 1, wherein receiving the scan of the patient's dentition comprises receiving an intraoral scan comprising one or more of: a near-infrared (near-IR) scan of the patient's dentition, an ultrasound scan of the patient's dentition, and an optical coherence tomography (OCT) scan of the patient's dentition.

4. The system of claim 1, further comprising scanning the patient's dentition with an intraoral scanner.

5. The system of claim 1, further comprising scanning the patient's dentition with an intraoral scanner to take a near-infrared (near-IR) scan of the patient's dentition.

6. The system of claim 1, wherein identifying further comprises identifying a location of one or more dental lesions and wherein determining one or more positions for orienting the x-ray apparatus comprises using the location of the one or more dental lesions to maximize an image of the one or more dental lesions in an x-ray image taken using the one or more positions.

7. The system of claim 1, wherein determining one or more positions for orienting an x-ray apparatus comprises determining a minimum number of x-ray images to take in order to capture images of all of the patient's teeth.

8. The system of claim 1, wherein guiding a user in taking one or more x-rays comprises determining a configuration for a bite block.

9. The system of claim 1, wherein guiding a user in taking one or more x-rays comprises robotically controlling the x-ray apparatus.

10. A system comprising:
    one or more processors;
    a memory coupled to the one or more processors, the memory configured to store computer-program instructions, that, when executed by the one or more processors, perform a computer-implemented method comprising:

receiving a scan of a patient's dentition, wherein the scan comprises a near-IR scan;

determining, a three-dimensional (3D) model of the patient's dentition based on the near-IR scan;

identifying, from the 3D model, tooth position and one or more of: a dental lesion and a dental restoration;

determining, using the 3D model, one or more positions for orienting an x-ray apparatus for x-raying a patient's teeth, including an identified dental lesion, in order to avoid interference from the dental restoration and/or an adjacent tooth; and guiding a user in taking one or more x-rays using the determined one or more positions for orienting an x-ray apparatus.

* * * * *